US005137014A

United States Patent [19]

Boehm

[11] Patent Number: 5,137,014

[45] Date of Patent: Aug. 11, 1992

[54] COIL FOR LITHOTRIPTER

[75] Inventor: Klaus Boehm, Munich, Fed. Rep. of Germany

[73] Assignee: Dornier Medizintechnik GmbH, Fed. Rep. of Germany

[21] Appl. No.: 591,294

[22] Filed: Oct. 1, 1990

[30] Foreign Application Priority Data

Sep. 30, 1989 [DE] Fed. Rep. of Germany ....... 3932745

[51] Int. Cl.[5] ........................................ A61B 17/22

[52] U.S. Cl. ........................ 128/24 EL; 367/175

[58] Field of Search .................. 128/24 EL; 181/142, 181/402, 113, 118; 367/141, 142, 174, 175

[56] References Cited

U.S. PATENT DOCUMENTS 4,807,627 2/1989 Eisenmenger .................. 128/24 EL
4,821,245 4/1989 Riedlinger ...................... 128/24 EL
4,901,709 2/1990 Rattner ......................... 128/24 EL
4,920,955 5/1990 Mahler et al. .................. 128/24 EL

*Primary Examiner*—Kyle L. Howell
*Assistant Examiner*—Scott R. Akers
*Attorney, Agent, or Firm*—R. H. Siegemund

[57] ABSTRACT

A lithotripter for the contactless comminution of concrements in living beings includes a flat coil cooperating with a juxtaposed membrane which upon energization of the coil produces shockwaves in an adjacent liquid, the liquid being in contact with the body of the living being, there being an insulation between the coil and the membrane, the coil having two or three parallely positioned wires for multiple windings with each winding having the same number of wires, and being electrically connected in parallel.

3 Claims, 2 Drawing Sheets

Fig. 1
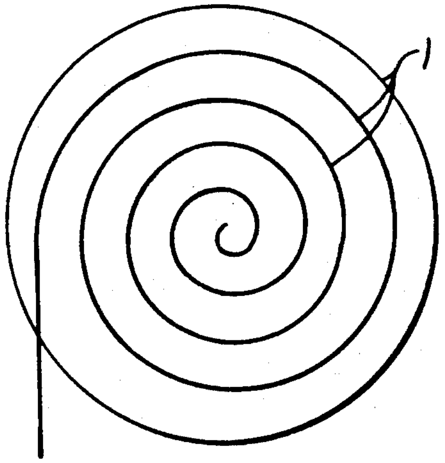
Fig. 2
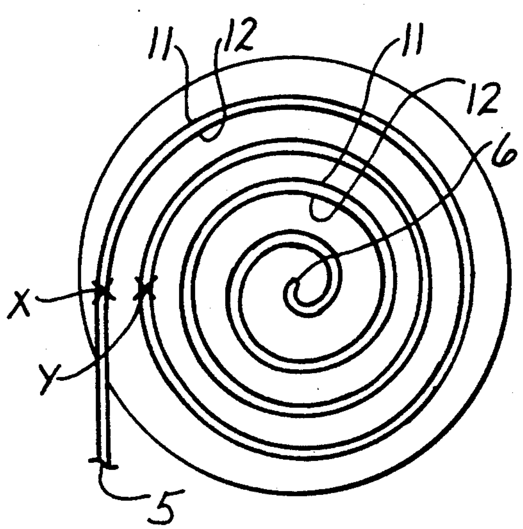
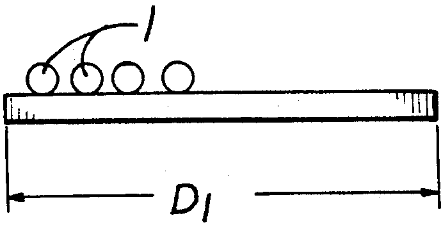
Fig. 1a
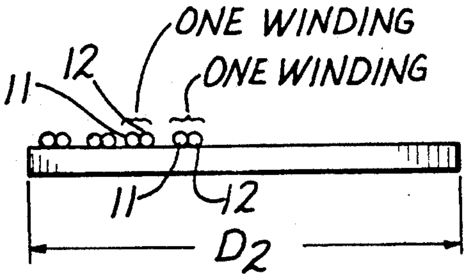
Fig. 2a

COIL FOR LITHOTRIPTER

BACKGROUND OF THE INVENTION

The present invention relates to a coil to be used in and being a component of a device for contactless noninvasive comminution of concrements in the body of a living being; such a device generally includes a shockwave generator that is oriented towards the target area in the body of said being; in one more specific configuration the generator includes a flat coil, cooperating with a membrane which in turn is positioned to provide vibrations into a liquid filled cavity whereby particularly a brief current pulse is applied to the coil and will cause the membrane to produce a shockwave.

European patent application EP 275427 describes and discloses a shockwave tube including a coil carrier made of a ceramic material. One front end of this coil carrier includes a flat coil being of a single wire configuration and being bonded to that front side by means of a synthetic resin. An insulating foil is disposed between the flat coil and the membrane whereby during manufacture the coil and the membrane are forced against each other to in fact establish a structural unity. As stated the single wire coil is spirally coiled and owing to its embedment in the synthetic resin an additional spacing is introduced between the outer surface of the wire and the membrane.

In order to provide a shockwave a short electric voltage pulse of high amplitude is applied to the coil, this energy originates from a capacitor that has been charged previously and is rapidly discharged into the coil. The resulting electromagnetic field causes the adjacent membrane to be pushed away in an impact fashion and that rapid displacement of the membrane produces a shockwave in the adjoining liquid. The insulating foil is simply provided in order to avoid a voltage breakthrough between the coil and the membrane since the membrane is made of metal. A maximization of the pressure for the shockwave is obtained by selecting the distance between the coil and the membrane as small as possible and the amplitude of the current pulse is as high as possible but for reasons of the insulation a certain spacing and certain insulation has to be maintained.

DESCRIPTION OF THE INVENTION

It is an object of the present invention to provide a new and improved coil for use in and as a part of a device of the kind described above, and particularly to related devices for the production of shockwaves with the goal in mind to increase the peak amplitude pressure of the ensuing shockwaves.

It is therefore a particular object of the present invention to provide a new and improved flat coil to be used in a device as a component thereof, for the comminution of concrements in the body of a living being under utilization of a shockwave generator of which the coil is a part and which cooperates with a metallic membrane juxtaposed to the coil but insulated therefrom.

In accordance with the preferred embodiment of the present invention it is suggested to provide the coil with a particular number of windings but in a multiple wire fashion as to each loop and winding whereby the individual wires run parallel per winding. The preferred embodiment will include just two or three wires per winding.

Therefore it can be seen that in lieu of the conventional single wire winding of the coil one uses a two or three wire coil with the same number of windings. The wires are wound spirally in parallel and in each case, one winding counts as a loop regardless of the number of participating wires. Owing to the small diameter of the wires the volume (V2 in the drawings) between respective two juxtaposed wires and the insulation between the wires and the membrane, and, therefore, the spacing of the coil as such from the membrane is reduced. This may seemingly be a very small improvement but in terms of operative gain it is significant. It was found that under such circumstances, all of the parameters being equal, the operating voltage can be increased and the pressure produced by the impulse deflection of the membrane is increased accordingly. On the other hand owing to the reduction in wire size, the volume space as between the current wires (in cross-section) and the flat insulation causes by itself an increase in the shockwave pressure since the pressure was found to be inversely proportional to the particular volume space. Other conditions being equal, on the other hand, the radius of the actually used wire is preferably 1/n of the corresponding radius of a single wire coil, with n being the number of wires per coil and winding. Preferably then the radius of the wires is one half or one third of a wire as if there were one per winding. Another aspect is that the multiwire winding reduces the inductivity of the coil and that is instrumental in producing a steeper rise in the current and that in turn is directly beneficial in the production of still higher shockwave pressure.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a somewhat schematic top view of a single wire coil in accordance with the state of the art;

FIG. 1*a* being somewhat schematical section view through that wire arrangement of FIG. 1.

FIGS. 2 and 2*a* are corresponding views but in this case with two coil wire in accordance with a preferred embodiment of the present invention;

FIG. 4 illustrates an enlarged section through the two type of coils, with FIG. 4*a* being applicable to FIGS. 1 and 1*a* while FIG. 4*b* being applicable to FIGS. 2 and 2*a*.

Proceeding now to the detailed description of the drawings, FIG. 1 illustrates a one or single wire coil in accordance with the state of the art. The coil is made up of a single wire 1 wound in four, inwardly spiralling loops and thus having four windings. The coil is flat and has an overall diameter D1. The number of windings as stated is four but more generally can be denoted, N with in this case N=4. The drawing is schematic in nature and the single wire 1 is represented by a single line. FIG. 1*a* illustrates somewhat more realistically a cross sectional view through the coil showing the wire thickness as it is applicable in this case. However the spacing between the wire loops is somewhat exaggerated, as will be explained shortly.

FIG. 2 is a first embodiment of the invention and shows a two wire coil, i.e. the coil is made up from two wires 11 and 12 strung in parallel. The loop from point x to point y represents one of the four two-wire windings. The term winding is understood to mean a loop of a near circular configuration (but for the gradual change in diameter on account of spiralling) which in this example comprises the two wires 11 an 12. As stated, together they are shown here to have four windings. The coil has a diameter D2 which may be the same as D1. The number of windings in general is N' which may be also equal to N, and in the present case N'=N=4. It can readily be seen that the individual wires 11 and 12 in the case of FIGS. 2 and 2*a* are considerably smaller in diameter; but they are connected electrically in parallel as indicated by the end connections 5 and 6.

FIGS. 3*a* and 3*b* illustrate, as stated respectively plane view and section view through a three wire coil. The coil here is made up from three wires 11, 12, and 13. These wires are strung together and again there ate four loops or windings, each winding consisting here of the three wires 11, 12, 13.

Turning now to FIGS. 4*a* and 4*b* they are enlarged crossections through wires as well as an insulation layer 2 and a membrane 4; the membrane is actuated by the respective coil when energized. In FIG. 4*a*, the single wire 1 has a diameter d1 with d1 being the diameter of the wire in each instance. The insulation 2 is situated between the coil and the membrane 4. V1 denotes the volume space between respective two wire loops and the insulation 2. Specifically, V1 is in crossection as illustrated established by two 90° arches pertaining to the same wire 1 but to adjacent loops or windings. In addition that space V1 is bounded by a straight line pertaining to the insulation 2

Turning now to FIG. 4*b* it shows the two wires 11 and 12 in the case of the coil as shown in FIGS. 2 and 2*a*. The diameter d2 of each of the two wires 11 and 12 is smaller than the diameter of d1. In the crossection of FIG. 4*b* the wires 11 and 12 alternate. One pair of crossection pertains to one loop or winding, the ones adjacent thereto pertain to another two wire winding etc. Owing to the juxtaposition of the wires and close abutment to each other and to the insulation, the volume V2 of space between respective two adjacent wires 11 and 12 and the insulation 2 is considerably smaller than the volume V1. This simple reduction in volume is a decisive factor in producing much higher pressure when on energization of the coil the membrane 4 is pushed away and into the liquid.

Figure 3:
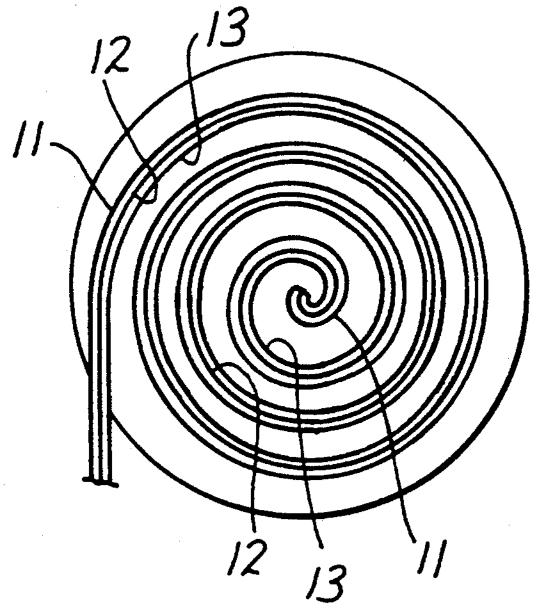
FIG. 3 and FIG. 3*a* are correspondingly view for a three-wire coil.
Figure 3A:
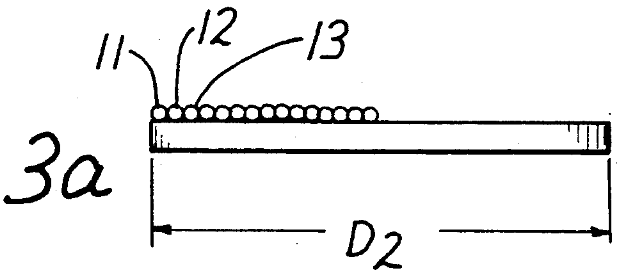
Figure 4A:
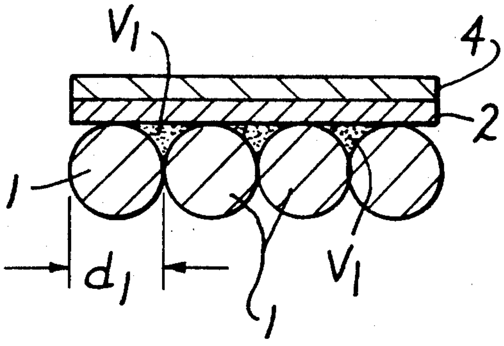
FIG. 4*a* shows the physical set up more realistically.
Figure 4B:
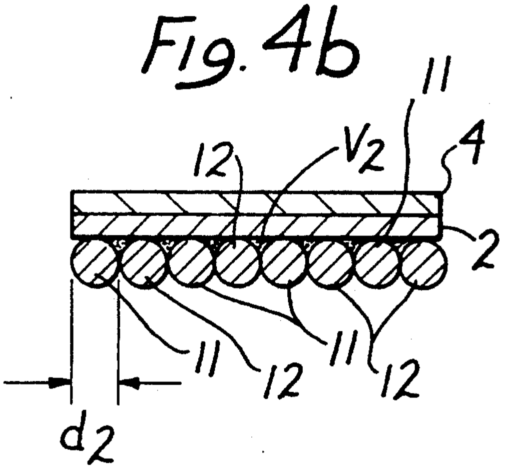

The invention is not limited to the embodiments described above but all changes and modifications thereof, not constituting departures from the spirit and scope of the invention, are intended to be included.

I claim:

1. In a lithotripter for the contactless comminution of concrements in a living being, the lithotripter including a flat coil for actuating a juxtaposed membrane, upon energization of the coil said membrane producing shockwaves in an adjacent liquid, the liquid adapted to be in contact with the body of the living being, there being an insulation between the coil and the membrane, the improvement comprising, the coil having a plurality of parallely positioned and juxtaposed, spirally wound wires for multiple windings with each winding having the same number of wires, said physically juxtaposed wires being electrically connected in parallel.

2. The lithotripter as in claim 1 there being two wires, so that there are two wires per winding.

3. The lithotripter as in claim 1, there being three wires, so that there are three wires per winding.

* * * * *